United States Patent
Vamvakides (10) Patent No.: US 9,180,106 B2
(45) Date of Patent: Nov. 10, 2015

(54) SIGMA RECEPTORS LIGANDS WITH ANTI-APOPTOTIC AND/OR PRO-APOPTOTIC PROPERTIES, OVER CELLULAR MECHANISMS, EXHIBITING PROTOTYPICAL CYTOPROTECTIVE AND ALSO ANTI-CANCER ACTIVITY

(71) Applicant: Anavex Life Sciences Corp., New York, NY (US)

(72) Inventor: Alexandre Vamvakides, Ymittos Attiki (GR)

(73) Assignee: Anavex Life Sciences Corp., New York, NY (US)

( * ) Notice: Subject to any disclaimer, the term of this patent is extended or adjusted under 35 U.S.C. 154(b) by 0 days.

(21) Appl. No.: 14/205,637

(22) Filed: Mar. 12, 2014

(65) Prior Publication Data
US 2014/0228375 A1 Aug. 14, 2014

Related U.S. Application Data

(63) Continuation of application No. 13/201,271, filed as application No. PCT/GR2010/000009 on Feb. 17, 2010, now abandoned.

(30) Foreign Application Priority Data

Feb. 26, 2009 (GR) .............. 20090100115

(51) Int. Cl.
*A61K 31/495* (2006.01)
*A61K 31/4453* (2006.01)
*A61K 31/137* (2006.01)
(Continued)

(52) U.S. Cl.
CPC ............... *A61K 31/137* (2013.01); *A61K 31/13* (2013.01); *A61K 31/341* (2013.01); *A61K 31/343* (2013.01); *A61K 31/365* (2013.01); *A61K 31/431* (2013.01); *A61K 31/44* (2013.01); *A61K 31/445* (2013.01); *A61K 31/4453* (2013.01); *A61K 31/4525* (2013.01);
(Continued)

(58) Field of Classification Search
None
See application file for complete search history.

(56) References Cited

U.S. PATENT DOCUMENTS

| 5,854,240 A | 12/1998 | Kupfer et al. |
| 6,482,986 B1 | 11/2002 | Boigegrain et al. |
| 2006/0019968 A1 | 1/2006 | Baeyens |

FOREIGN PATENT DOCUMENTS

| FR | 2897535 A1 | 8/2007 |
| GR | 1004208 B1 | 4/2003 |

(Continued)

*Primary Examiner* — Anna Pagonakis
(74) *Attorney, Agent, or Firm* — Novak Druce Connolly Bove + Quigg LLP (57) ABSTRACT

The present invention involves new and original sigma receptors ligands: (Mono- or dialkylaminoalkyl)-γ-butyrolactones, their analogues aminotetrahydroturanes, the (1-adamantyl) benzene alkylamines, the N,N Dialkyl α-[(adamantyl-1)benzyloxy-2]alkylamines and the 3-cyclopentyl adamantyl-amines or alkylamines or -alkyl phenylamines, their enantiomers or diastereoisomers, their pharmaceutically acceptable salts and Quinacrine Me-thylene blue, Asteinizole and their relative analogues with pro-apoptotic and/or anti-apoptotic properties over cellular biochemical mechanisms, with prototypical anti-cancer, antimetastatic and antiviral activities associated with antagonism of the neuropatic pain and, at very low doses, with cytoprotective and cytoregenerative activity against the cytodegenerative diseases.

16 Claims, 12 Drawing Sheets

(51) Int. Cl.
| | |
|---|---|
| *A61K 31/365* | (2006.01) |
| *A61K 31/13* | (2006.01) |
| *A61K 31/341* | (2006.01) |
| *A61K 31/343* | (2006.01) |
| *A61K 31/431* | (2006.01) |
| *A61K 31/44* | (2006.01) |
| *A61K 31/445* | (2006.01) |
| *A61K 31/5377* | (2006.01) |
| *A61K 31/5415* | (2006.01) |
| *A61K 31/64* | (2006.01) |
| *A61K 31/4525* | (2006.01) |

(52) U.S. Cl.
CPC .......... *A61K 31/495* (2013.01); *A61K 31/5377* (2013.01); *A61K 31/5415* (2013.01); *A61K 31/64* (2013.01)

(56) References Cited

FOREIGN PATENT DOCUMENTS

| | | |
|---|---|---|
| GR | 2003100190 A | 12/2004 |
| WO | 9730983 A1 | 8/1997 |
| WO | 2006012419 A2 | 2/2006 |
| WO | 2007025613 A2 | 3/2007 |
| WO | 2008087458 A2 | 7/2008 |

APPENDIX

| Structure | Name | Melting Point (m.p) |
|---|---|---|
|  | 1-[4-[(1-Adamantyl)phenylmethyl]-1-phenyl]-4-methylpiperazine chloridrate | 277-279°C |
|  | 1-[4-[(1-Adamantyl)phenylmethyl]-1-phenyl]-4-methylpiperazine bichloridrate | 287-290°C |
|  | 1-[a-(1-Adamantyl)diphenylmethyl] 4-methylpiperazine bichloridrate | 156-158°C |
|  | 1-[4-(1-Adamantyl)-4,4-diphenylbut-1-yl]4-methylpiperazine bichloridrate | 263-265°C |

FIG. 1

| Structure | Name | Melting Point (m.p) |
|---|---|---|
|  | 1-[4-(1-Adamantyl)-4,4-diphenylbut-1-yl]-4-ethylpiperazine bichloridrate | 261-263°C |
|  | 1-[4-(1-Adamantyl)-4,4-diphenylbut-1-yl]-piperidine chloridrate | 286-288°C |
|  | 1-[4-(1-Adamantyl)-4,4-diphenylbut-1-yl]-4-cyclohexyl piperazine bichloridrate | 260-262°C |
|  | 4-(1-Adamantyl)-N,N-dimethyl-4,4-diphenyl-1-butylamine chloridrate | 261-263°C |

FIG. 2

| Structure | Name | Melting Point (m.p) |
|---|---|---|
| (structure: adamantyl-CH(phenyl)-phenyl-propyl-N-methylpiperazine · 2HCl) | 1-[3-[4-[α-(1-Adamantyl)phenylmethyl]phenyl]-1-propyl]-4-methylpiperazine bichloridrate | 273-275°C (dec.) |
| (structure: adamantyl-CH(phenyl)-butyl-piperidine · HCl) | 1-[4-(1-Adamantyl)-4-phenyl-but-1-yl]piperidine chloridrate | 230-232°C |
| (structure: adamantyl-C(phenyl)=CH-CH2-N-piperidine-4-OH · HCl) | 1-[3-[(1-Adamantyl)-3-phenyl-2-propen-1-yl]-4-hydroxy piperidine chloridrate | 245-248°C |
| (structure: adamantyl-CH(phenyl)-CH2-CH2-N-methylpiperazine · 2HCl) | 1-[3-[(1-Adamantyl)-3-phenyl-1-propyl]-4-methylpiperazine | 298-300°C |
| (structure: adamantyl-C(phenyl)=CH-CH2-N-methylpiperazine · 2HCl) | 1-[3-(1-Adamantyl)-3-phenylprop-2-enyl]-4-methylpiperazine bishydrochloride | 281-283 °C (decomp.) |

FIG. 3

| Structure | Name | Melting Point (m.p) |
|---|---|---|
|  | 1-[4-(1-Adamantyl)-4-phenyl-3-buten-1-yl] piperidine hydrochloride | 230-231 °C |
|  | 1-[5-(1-Adamantyl)-5-phenyl-4-penten-1-yl] piperidine hydrochloride | 215-217 °C (dec.) |
|  | 1-[5-(1-Adamantyl)-5-phenyl-4-penten-1-yl]-4-methyl piperazine bishydrochloride | 268-270 °C (dec.) |
|  | 1-[4-(1-Adamantyl)-4-phenyl-1-butyl]-4-methylpiperazine bishydrochloride | 275-277 °C (decomp.) |

FIG. 4

| Structure | Name | M.p. |
|---|---|---|
|  | 1-[5-(1-Adamantyl)-5-phenyl-1-pentyl] piperidine hydrochloride | 220-221 °C |
|  | 1-[5-(1-Adamantyl)-5-phenyl-1-pentyl]-4-methylpiperazine bishydrochloride | 260-262 °C (decomp.) |
|  | 6-(1-Adamantyl)-N,N-dimethyl-6-phenyl-5-hexen-1-amine hydrochloride | 193-195 °C |
|  | 1-[6-(1-Adamantyl)-6-phenyl-5-hexen-1-yl]-4-methyl piperazine hydrochloride | 246-248 °C |
|  | 1-[6-(1-Adamantyl)-6-phenyl-5-hexen-1-yl]-piperidine hydrochloride | |

FIG. 5

| Structure | Name | |
|---|---|---|
|  | 6-(1-Adamantyl)-N,N-dimethyl-6-phenyl-1-hexylamine hydrochloride | |
|  | 1-[6-(1-Adamantyl)-6-phenyl-1-hexyl]-piperidine hydrochloride | |
|  | 3-Dimethylaminomethyl-5-(4-chlorophenoxy methyl) diphenyldihydrofuran-2(3H)-one hydrochloride | 181-182°C |
|  | 1-[4-[(3-Cyclopentyl-1-adamantyl)phenylmethyl]-1-phenyl]-4-methylpiperazine hydrochloride | 229-231°C |
|  | 1-[4-[(3-Cyclopentyl-1-adamantyl)phenylmethyl]-1-phenyl]-4-ethylpiperazine bishydrochloride | 229-231°C |

FIG. 6

| | | |
|---|---|---|
|  | 1-[4-[(3-Cyclopentyl-1-adamantyl)phenylmethyl]-1-phenyl]-4-cyclohexylpiperazine hydrochloride | 149-151 °C |
| | | |
|  | 5-(3-Cyclopentyltricyclo[3.3.1.1$^{3,7}$]dec-1-yl)-dihydro-3-(di methylaminomethyl)-5-phenylfuran-2(3H)-one hydrochloride | 210-213°C |
|  | 5-(3-Cyclopentyltricyclo[3.3.1.1$^{3,7}$]dec-1-yl)-tetrahydro-N,N-dimethyl-5-phenyl-3-furanemethylamine hydrochloride | 234-236 °C (dec.) |
|  | 5-(3-Cyclopentyltricyclo[3.3.1.1$^{3,7}$]dec-1-yl)-dihydro-3-(methylaminomethyl)-5-phenylfuran-2(3H)-one hydrochloride | |

FIG. 7

| | | |
|---|---|---|
| | 5-(3-Cyclopentyltricyclo[3.3.1.1$^{3,7}$]dec-1-yl)-dihydro-3-(di methylaminomethyl)-5-phenylfuran-2(3H)-one hydrochloride | 210-213°C |
| | 5,5-Diphenyl-N-[2-(1-phenylmethyl-4-piperidinyl)ethyl]tetrahydrofurane-3-carboxamide chloridrate | 173-176°C (dec) |
| | Bis-(5-(4-Chlorophenoxymethyl)-N,N-diethyl-tetrahydrofuran-3-aminomethyl) fumarate | 93-95 °C |
| | 5-(4-Chlorophenoxymethyl)-N,N-dimethyl-tetrahydrofurane-3-methylamine hydrochloride | 129-131°C |

FIG. 8

| Structure | Name | M.P. |
|---|---|---|
| (fluorene spiro furan with CH₂N(CH₃)₂·HCl) | 3',4'-Dihydro-N,N-dimethylspiro[9H-fluorene-9,2'(5'H)-furane]-3'-methanamine hydrochloride | 254-255°C(dec) (lit. 261°C) |
| (di(4-chlorophenyl) tetrahydrofuran with CH₂NHCH₃·HCl) | Tetrahydro-2,2-di(4-chlorophenyl)-N-methyl-3-furanemethan amine hydrochloride | 129-130 °C |
| (di(4-chlorophenyl) tetrahydrofuran with CH₂N(CH₃)₂·HCl) | Tetrahydro-2,2-di(4-chlorophenyl)-N,N-dimethyl-3-furane methanamine hydrochloride | 121-122 °C |
| (adamantyl phenyl tetrahydrofuran with CH₂N(CH₂CH₃)₂·HCl) | 5-(Tricyclo[3.3.1.1$^{3,7}$]dec-1-yl)-tetrahydro-N,N-diethyl-5-phenyl-3-furanemethanamine hydrochloride | 212-213°C |

FIG. 9

| Structure | Name | Melting Point (m.p) |
|---|---|---|
| (adamantyl-phenyl-tetrahydrofuran-methylpiperidine, HCl) | 5-(Tricyclo[3.3.1.1³,⁷]dec-1-yl)-tetrahydro-5-phenyl-3-furane methylpiperidine hydrochloride | around 275 °C (decomp.) |
| (dihydrospiro[fluorene-furane]-methanamine, HCl) | 3',4'-Dihydro-N,N-dimethylspiro[9H-fluorene-9,2'(5'H)-furane]-4'-methanamine hydrochloride | 252-254°C |
| Ph, Ph, O (−) (diphenyl tetrahydrofuran dimethylaminomethyl, HCl) | 5,5-Diphenyl-N,N-dimethyltetrahydrofuranemethanamine hydrochloride | 238-239°C |

| Structure | Name | Melting Point (m.p) |
|---|---|---|
| Ph, Ph, O (+) (diphenyl tetrahydrofuran dimethylaminomethyl, HCl) | 5,5-Diphenyl-N,N-dimethyltetrahydrofuranemethanamine hydrochloride | 238-239°C |
| Ph, Ph, O (+) (2,2-diphenyl tetrahydrofuran-3-methyl dimethylamine, HCl) | Tetrahydro-N,N-dimethyl-2,2-diphenyl-3-furanemethanamine hydrochloride | 226-228°C (lit. 224-224°C) |

FIG. 10

| Structure | Name | Melting Point (m.p) |
|---|---|---|
| (structure: tetrahydrofuran with 2,2-diphenyl and 3-CH2N(CH3)2·HCl, (−)) | Tetrahydro-N,N-dimethyl-2,2-diphenyl-3-furanemethanamine hydrochloride | 226-228°C (lit. 224-224°C) |
| (structure: spiro fluorene-furanone with CH2N(CH3)2·HCl) | 3',4'-Dihydro-3'-(dimethylaminomethyl)spiro[9H-fluorene-9,2'(5'H)-furan]-5'-one hydrochloride | 253-254°C (lit. 256-257°C) |
| (structure: 4-chlorophenoxymethyl dihydrofuranone with CH2N(CH3)2·HCl) | 3-Dimethylaminomethyl-5-(4-chlorophenoxy methyl)diphenyldihydrofuran-2(3H)-one hydrochloride | 181-182°C |

| Structure | Name | Melting Point (m.p) |
|---|---|---|
| (structure: adamantyl-phenyl tetrahydrofuran with CH2NH(CH3)·HCl) | 5-(Tricyclo[3.3.1.1^{3,7}]dec-1-yl)-tetrahydro-N-methyl-5-phenyl-3-furanemethanamine hydrochloride | 228-229°C |

FIG. 11

| | | |
|---|---|---|
|  | 5-(Tricyclo[3.3.1.1³,⁷]dec-1-yl)-dihydro-3-(methylamino methyl)-5-phenylfuran-2(3H)-one hydrochloride | |
|  | 5-(Tricyclo[3.3.1.1³,⁷]dec-1-yl)-dihydro-3-(1-piperidino methyl)-5-phenylfuran-2(3H)-one hydrochloride | 213-215°C |
|  | 3-(2-Diethylaminoethyl)-5,5-diphenyldihydrofuran-2(3H)-one hydrochloride | 164-166°C |

FIG. 12 US 9,180,106 B2

SIGMA RECEPTORS LIGANDS WITH ANTI-APOPTOTIC AND/OR PRO-APOPTOTIC PROPERTIES, OVER CELLULAR MECHANISMS, EXHIBITING PROTOTYPICAL CYTOPROTECTIVE AND ALSO ANTI-CANCER ACTIVITY

CROSS-REFERENCE TO RELATED APPLICATIONS

This application is a continuation and claims priority to co-pending U.S. Ser. No. 13/201,271, filed Aug. 12, 2011, which is a U.S. national phase application under 35 U.S.C. §371 based upon co-pending International Application No. PCT/GR2010/000009 filed on Feb. 17, 2010. Additionally, this U.S. national phase application claims the benefit of priority of co-pending International Application No. PCT/GR2010/000009 filed on Feb. 17, 2010, and Greece Application No. 20090100115 filed on Feb. 26, 2009, all commonly owned and having common inventorship. The entire disclosures of the prior applications are incorporated herein by reference. The international application was published on Sep. 2, 2010 under Publication No. WO 2010/097641.

BACKGROUND OF THE INVENTION

Field of the Invention

The present invention relates to sigma(a) receptors ligands with anti-apoptotic and/or pro-apoptotic properties for use in connection with exhibiting prototypical cytoprotective properties associated with cytoregenerative activity developed by antagonism of the endoplasmic reticulum stress (ER stress) via activation of the sigma receptors in the connecting membrane between ER and mitochondrion.

SUMMARY OF THE INVENTION

In view of the foregoing disadvantages inherent in the prior art, the present invention provides an improved sigma(a) receptor ligands and method for using, and overcomes the above-mentioned disadvantages and drawbacks of the prior art. As such, the general purpose of the present invention, which will be described subsequently in greater detail, is to provide a new and improved sigma(a) receptor ligands and method which has all the advantages of the prior art mentioned heretofore and many novel features that result in a sigma(a) receptor ligands which is not anticipated, rendered obvious, suggested, or even implied by the prior art, either alone or in any combination thereof.

To attain this, the present invention essentially comprises a method for using a compound including sigma(a)-receptor ligands and a sigma(a) ligands generics. The method includes the providing of a compound having a sigma(a)-receptor ligands and a sigma(a) ligands generics, wherein the sigma(a) ligands generics is selected from Quinacrine, analogues of Quinacrine, Methylene blue, analogues of Methylene blue, Astemizole, and analogues of Astemizole. Then method further includes using the composition for the preparation of pharmaceuticals.

The pharmaceuticals have anticancer, antimetastatic and antiviral activity associated with analgesic properties.

The sigma(a)-receptor ligands may also be selected from (mono- or dialkylaminoalkyl)-γ-butyrolactones), aminotetrahydrofuranes, enantiomers or diastereoisomers of aminotetrahydrofuranes, (1-adamantyl)benzene alkylamines, enantiomers or diastereoisomers of (1-adamantyl)benzene alkylamines, N,N di-alkyl a[(adamantyl-1)benzyloxy-2] alkylamines, enantiomers or diastereoisomers of N,N dialkyl a-[(adamantyl-1)benzyloxy-2]alkylamines, 3-cyclopentyl adamantyl-amines or -alkylamines or -alkyl phenylamines, enantiomers or diastereoisomers of 3-cyclopentyl adamantyl-amines or -alkylamines or -alkyl phenylamines, and their pharmaceutically acceptable salts.

There has thus been outlined, rather broadly, the more important features of the invention in order that the detailed description thereof that follows may be better understood and in order that the present contribution to the art may be better appreciated.

The invention may also include the preparation of pharmaceuticals having analgesic activity against neuropathic pain, acting synergistically with clinically used anticancer drugs and antagonizing neuropathic pain induced by the anticancer drugs, pharmaceuticals with cytoprotective activity against pathogenesis of cytodegenerative diseases, pharmaceuticals with cytoprotective and cytoregenerative activity, and pharmaceuticals with protective activity against the pathogenesis of inflammatory and neuropathic pain. There are, of course, additional features of the invention that will be described hereinafter and which will form the subject matter of the claims attached.

Numerous objects, features and advantages of the present invention will be readily apparent to those of ordinary skill in the art upon a reading of the following detailed description of present, but nonetheless illustrative, embodiments of the present invention. In this respect, before explaining the current embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION OF THE INVENTION

DETAILED DESCRIPTION OF THE PREFERRED EMBODIMENTS

Figure 1:
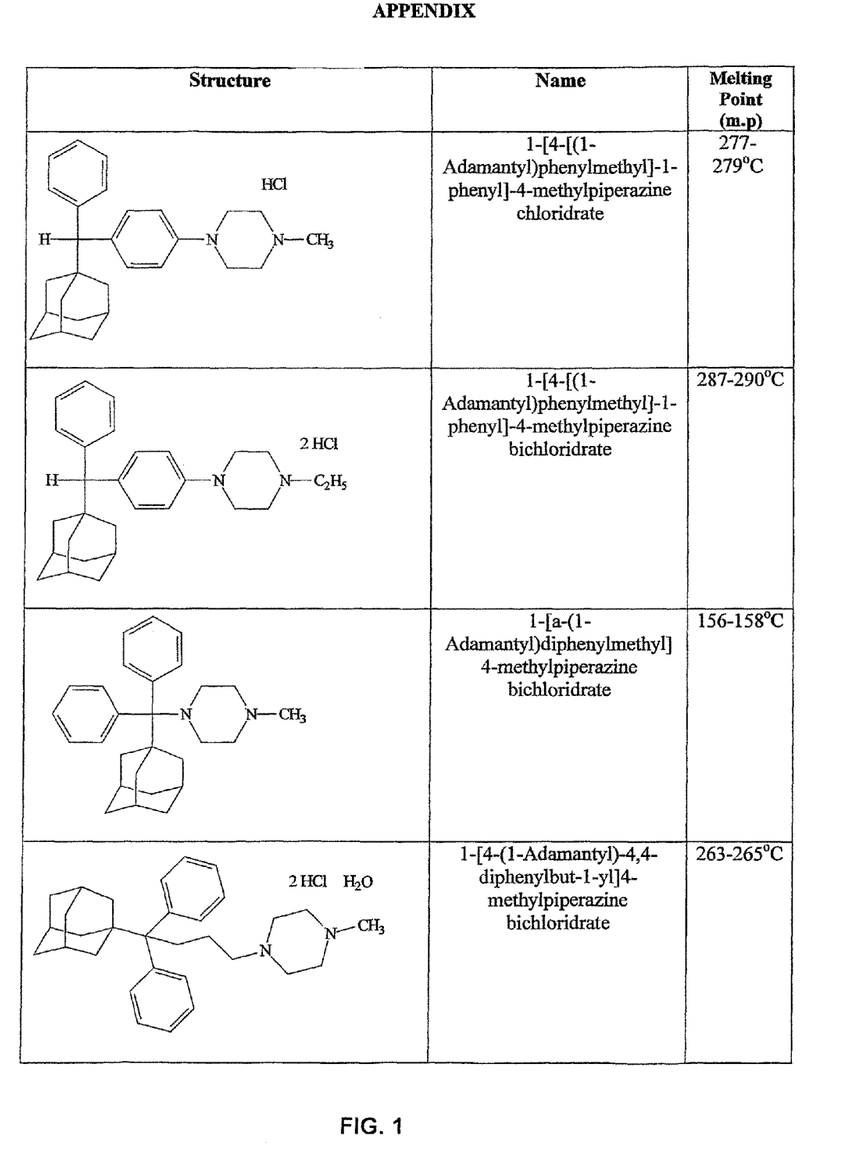
FIG. 1 is a structural representation of 1-[4-[(1-Adamantyl)phenylmethyl]-1-phenyl]-4-methylpiperazine chloridrate, 1-[4-[(1-Adamantyl)phenylmethyl]-1-phenyl]-4-methylpiperazine bichloridrate, 1-[a-(1-Adamantyl)diphenylmethyl]4-methylpiperazine bichloridrate, and 1-[4-[(1-Adamantyl)-4,4-diphenylbutl-1-yl]4-methylpiperazine bichloridrate.
Figure 2:
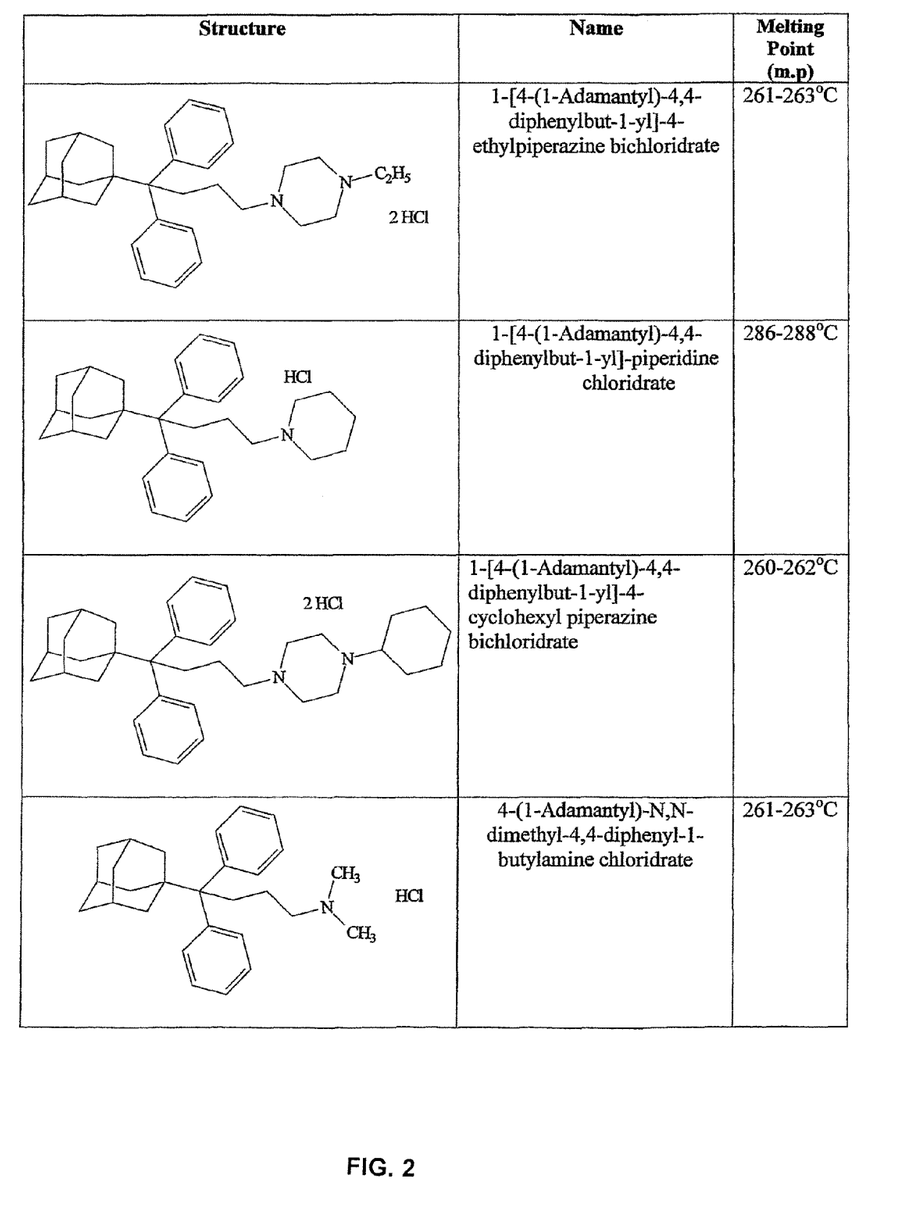
FIG. 2 is a structural representation of 1-[4-[(1-Adamantyl)-4,4-diphenylbut-1-yl)-4-ethylpiperazine bichloridrate, 1-[4-[(1-Adamantyl)-4,4-diphenylbut-1-yl]-piperidine chloridrate, 1-[4-[(1-Adamantyl)-4,4-diphenylbut-1-yl]-4-cyclohexyl piperazine bichloridrate, and 4-[(1-Adamantyl)-N,N-dimethyl-4,4-diphenyl-1-butylamine chloridrate.
Figure 3:
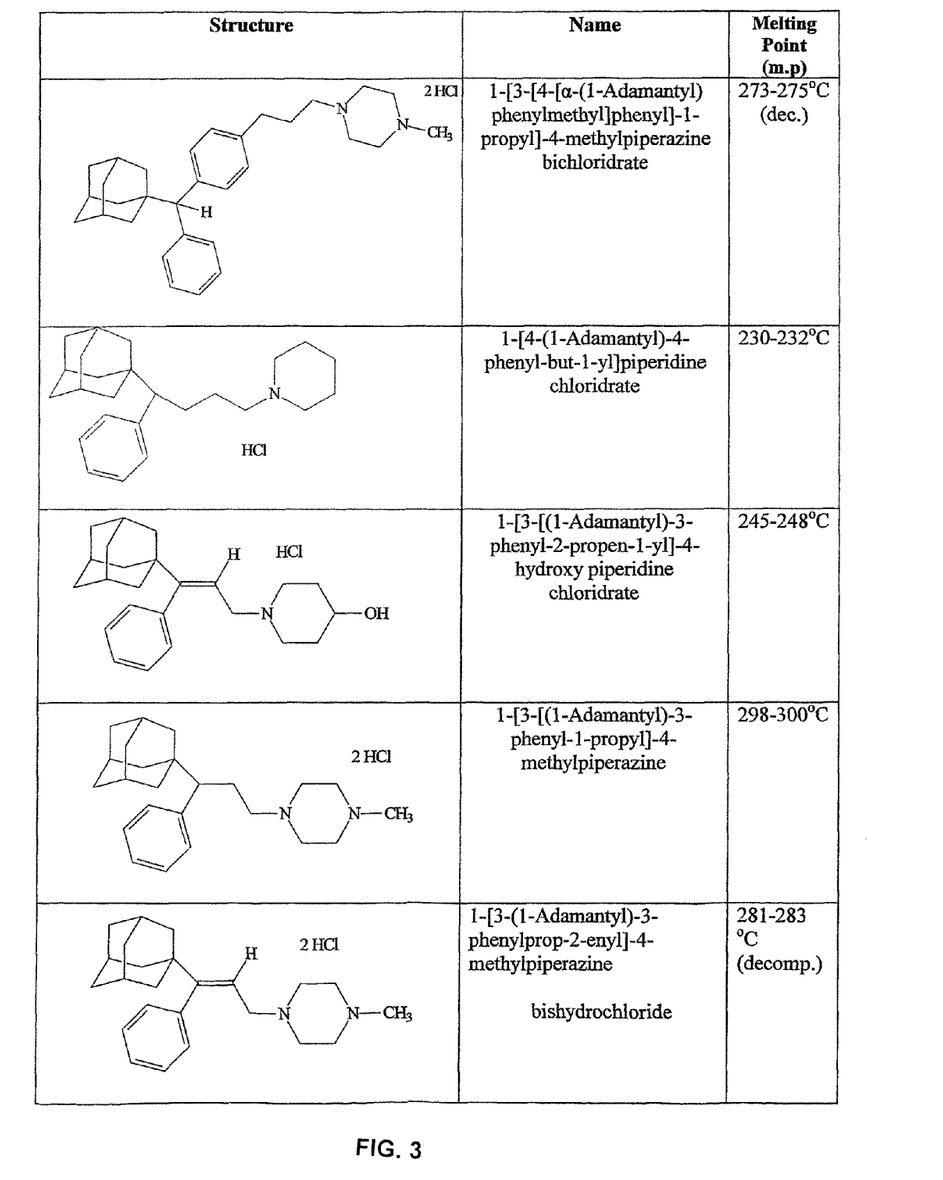
FIG. 3 is a structural representation of 1-[3-[4-[α-(1-Adamantyl)phenylmethyl]phenyl]-1-propyl]-4-methylpiperazine bichlordrate, 1-[4-(1-Adamantyl)-4-phenyl-but-1yl]piperidine chloridrate, 1-[3-[(1-Adamantyl)-3-phenyl-2-propen-1-yl]-4-hydroxy piperidine chloridrate, 1-[3-[(1-Adamantyl)-3-phenyl-1-propyl]-4-methylpiperazine, 1-[3-(1-Adamantyl)-3-phenylprop-2-enyl]-4-methylpiperazine bishydrochloride.
Figure 4:
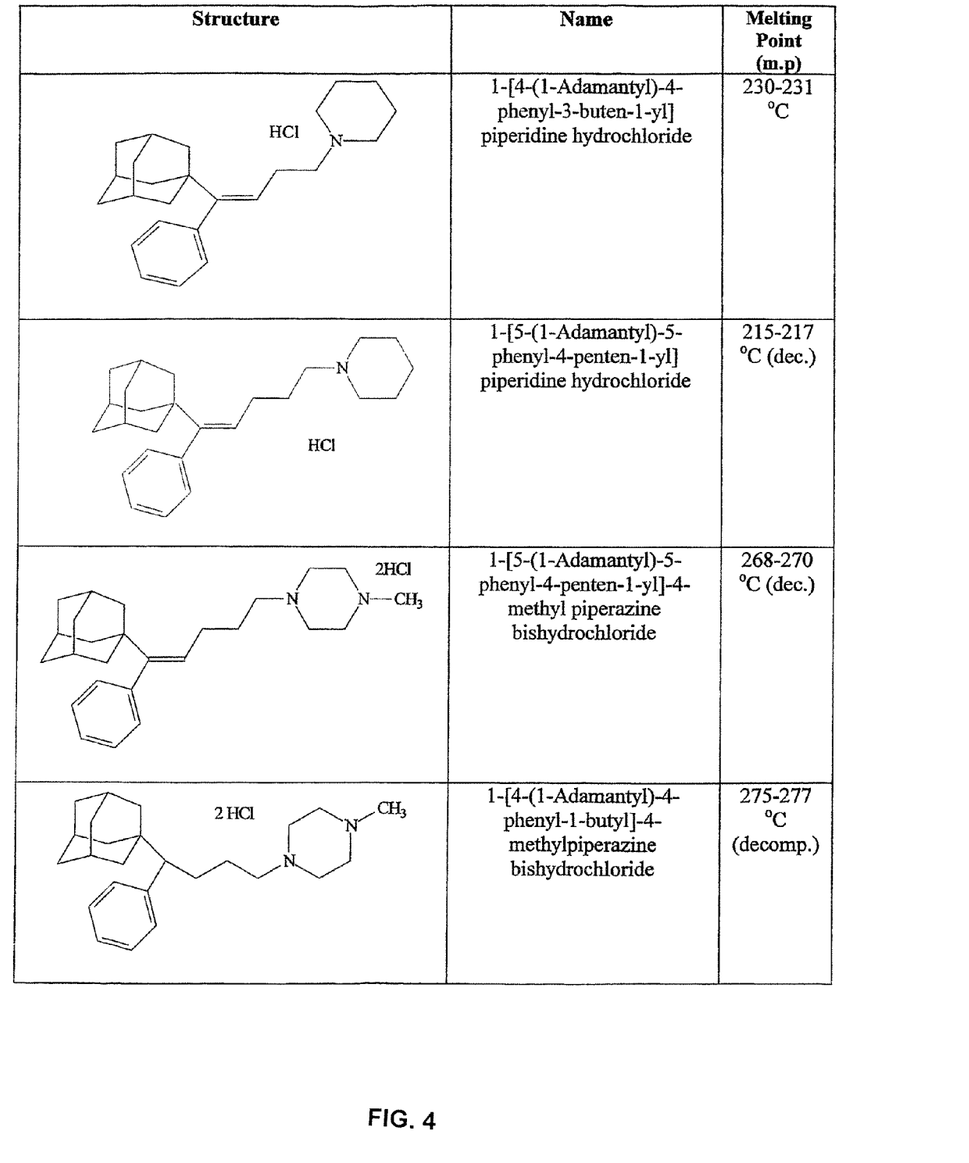
FIG. 4 is a structural representation of 1-[4-(1-Adamantyl)-4-phenyl-3-buten-1-yl]piperidine hydrochloride, 1-5[-(1-Adamantyl)-5-phenyl-4-penten-1-yl]piperidine hydrochloride, 1-[5-(1-Adamantyl)-5-phenyl-4-penten-1-yl]-4-methyl piperazine bishydrochloride, 1-[4-(1-Adamantyl)-4-phenyl-1-butyl]-4-methylpiperazine bishydrochloride.
Figure 5:
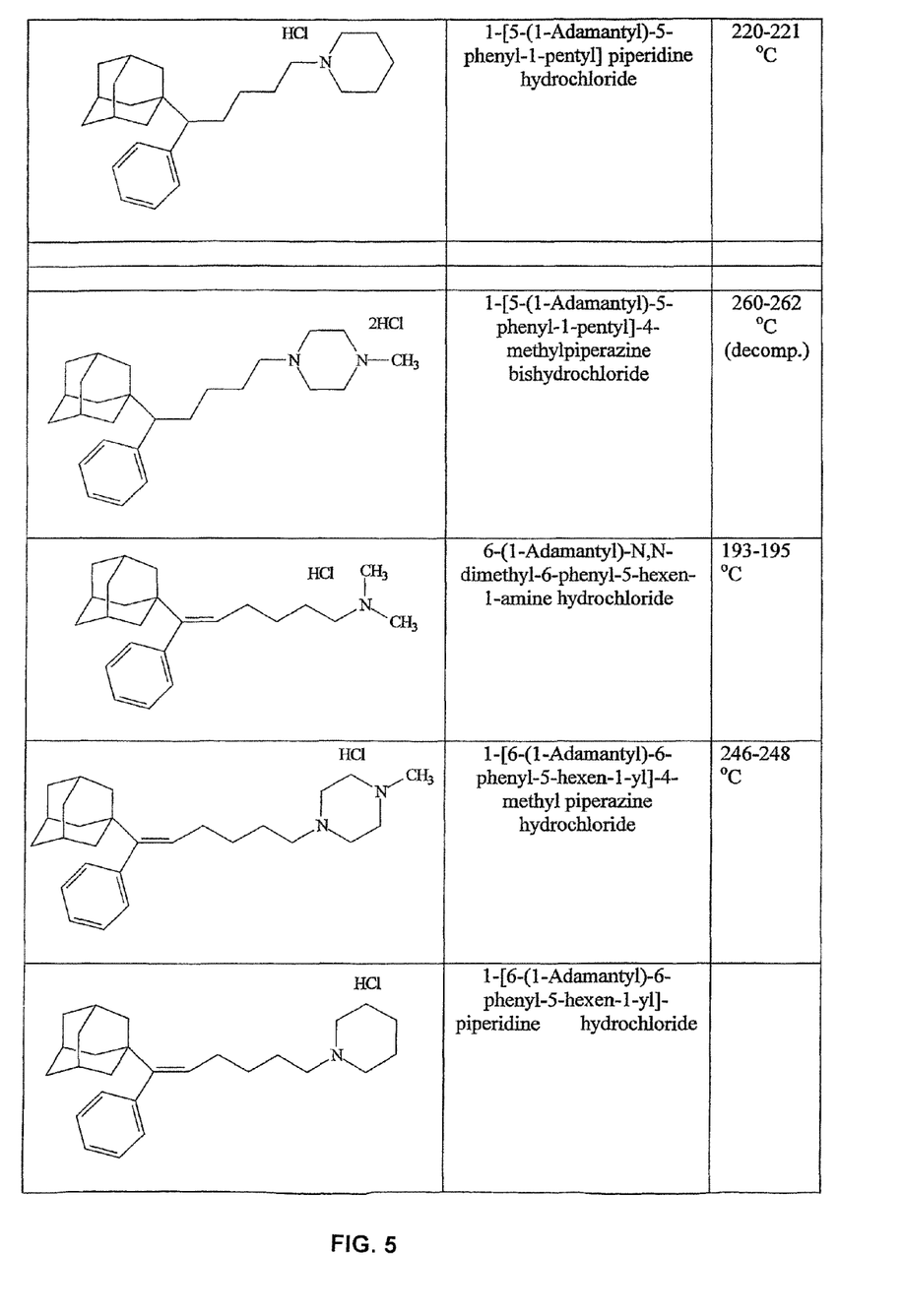
FIG. 5 is a structural representation of 1-[5-(1-Adamantyl)-5-phenyl-1-pentyl]piperidine hydrochloride, 1-[5-(1-Adamantyl)-5-phenyl-1-entyl]-4-methylpiperazine bishydrochloride, 6-1(1-Adamantyl)-N,N-dimethyl-6-phenyl-5-hexen-1-amine hydrochloride, 1-[6-(1-Adamantyl)-6-phenyl-5-hexen-1-yl]-4-methyl piperazine hydrochloride, 1-[6-(1-Adamantyl)-6-phenyl-5-hexen-1-yl]-piperidine hydrochloride.
Figure 6:
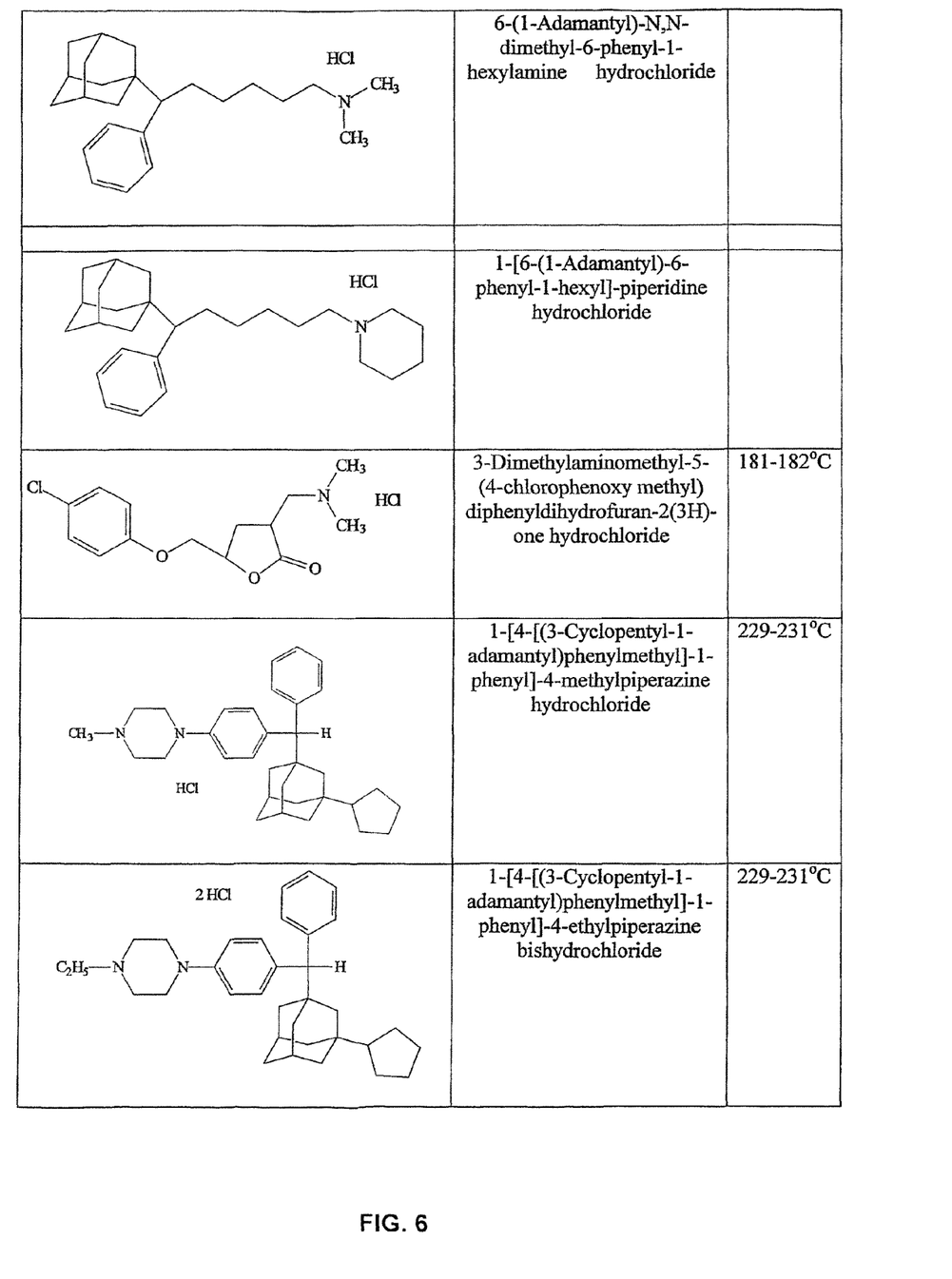
FIG. 6 is a structural representation of 6-(1-Adamantyl)-N,N-dimethyl-6-phenyl-1-hexylamine hydrochloride, 1-[6-(1-Adamantyl)-6-phenyl-1-hexyl]-piperidine hydrochloride, 3-Dimethylaminomethyl-5-(4-chlorophenoxy methyl) diphenyldihydrofuran-2(3H)-one hydrochloride, 1-[4-[(3-Cyclopentyl-1-adamantyl)phenylmethyl]-1-phenyl]-4-methylpiperazine hydrochloride, 1-[4-[(3-Cyclopentyl-1-adamantyl)phenylmethyl]-1-phenyl]-4-ethylpeperazine bishydrochloride.
Figure 7:
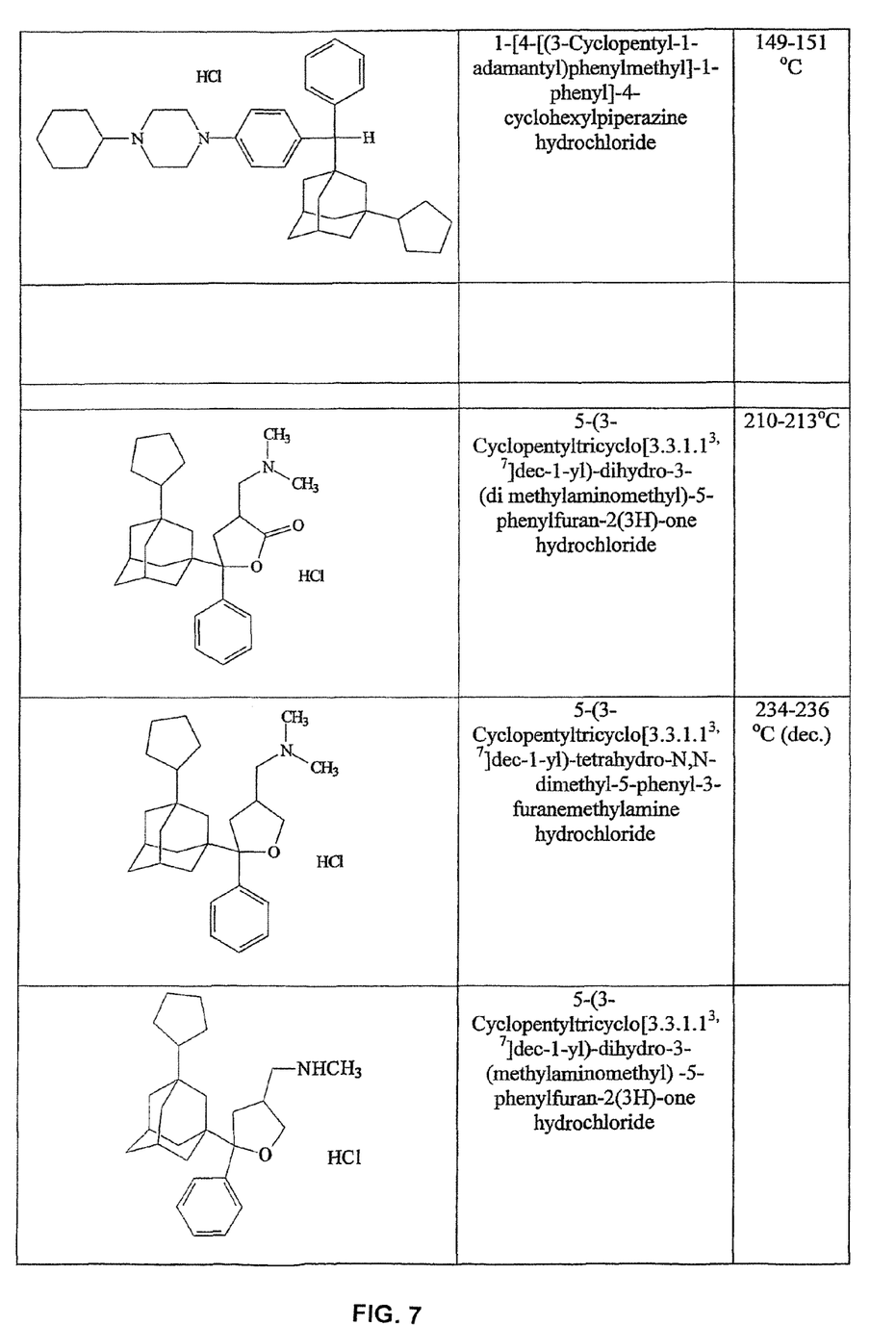
FIG. 7 is a structural representation of 1-[4-[4-(3-Cyclopentyl-1-adamantyl)phenylmethyl]-1-henyl]-4-cyclohexylpiperazine hydrochloride, 5-3-Cyclopentricyclo[3.3.1.1$^{3,7}$]dec-1-yl]-dihydro-3-(dimethylamino)-5-phenylfuran-2(3H)-one hydrochloride, 5-(3-Cyclopentyltricyclo[3.3.1.1$^{3,7}$]dec-1-yl)-tetrahydro-N,N-dimethyl-5-phenyl-3-furanemethylamine hydrochloride, 5-(3-Cyclopentyltricyclo[3.3.1.1$^{3,7}$]dec-1-yl)-dihydro-3-(methylaminomethyl)-5-phenylfuran-2(3H)-one hydrochloride.
Figure 8:
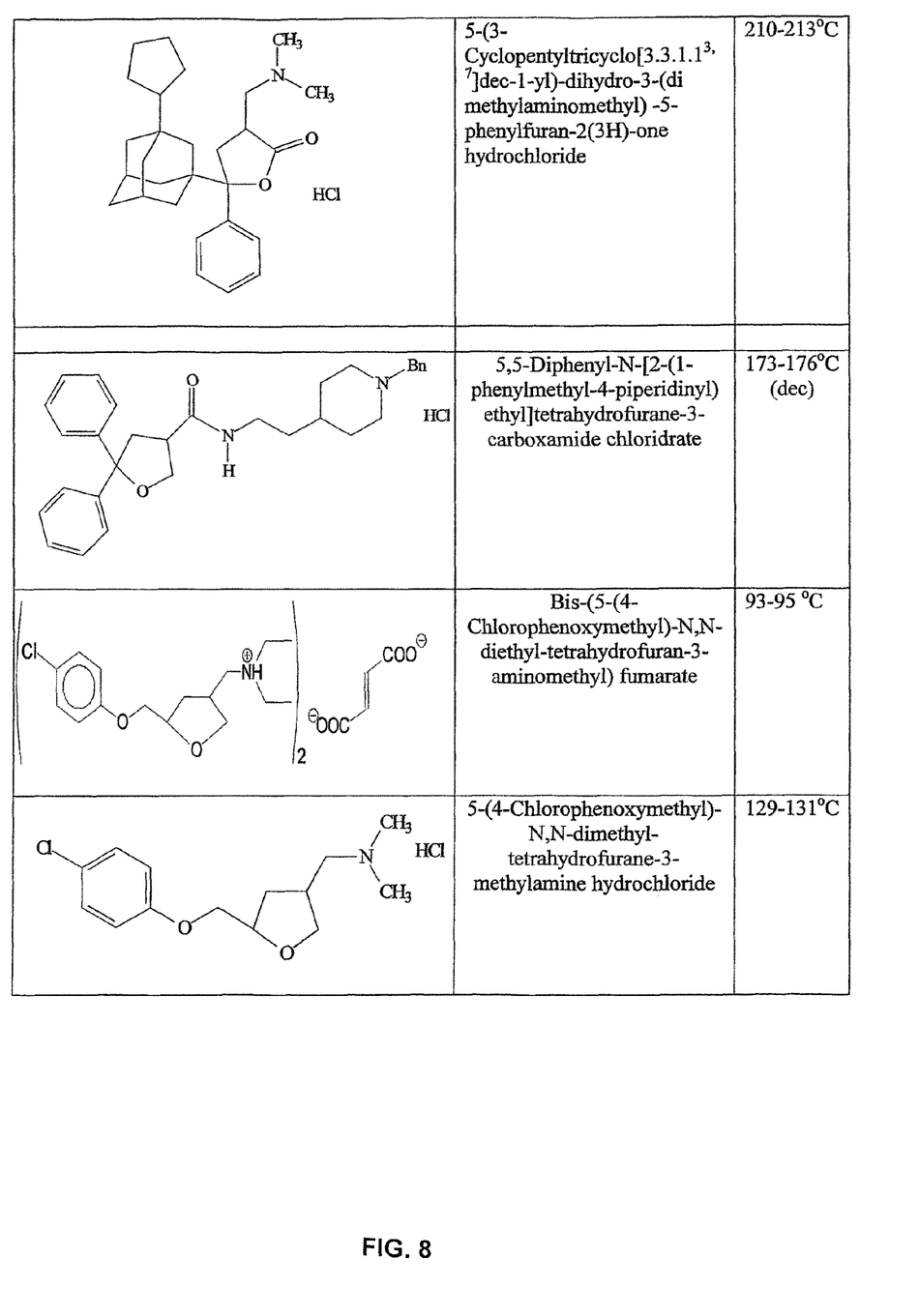
FIG. 8 is a structural representation of 5-(3-Cyclopentyltricyclo[3.3.1.1$^{3,7}$]dec-1-yl)-dihydro-3-(dimethylaminomethyl)-5-phenylfuran-2(3H)-one hydrochloride, 5,5-Diphenyl-N-[2-(1-phenylmethyl-4-piperidinyl)ethyl]tetrahydrofurane-3-carboxamide chloridrate, Bis-(5-(4-CHlorophenoxymethyl)-N,N-diethyl-tetrahydrofuran-3-aminomethyl) fumarate, 5-(4-Chlorophenoxymethyl)-N,N-dimethyl-tetrahydrofurane-3-methylamine hydrochloride.
Figure 9:
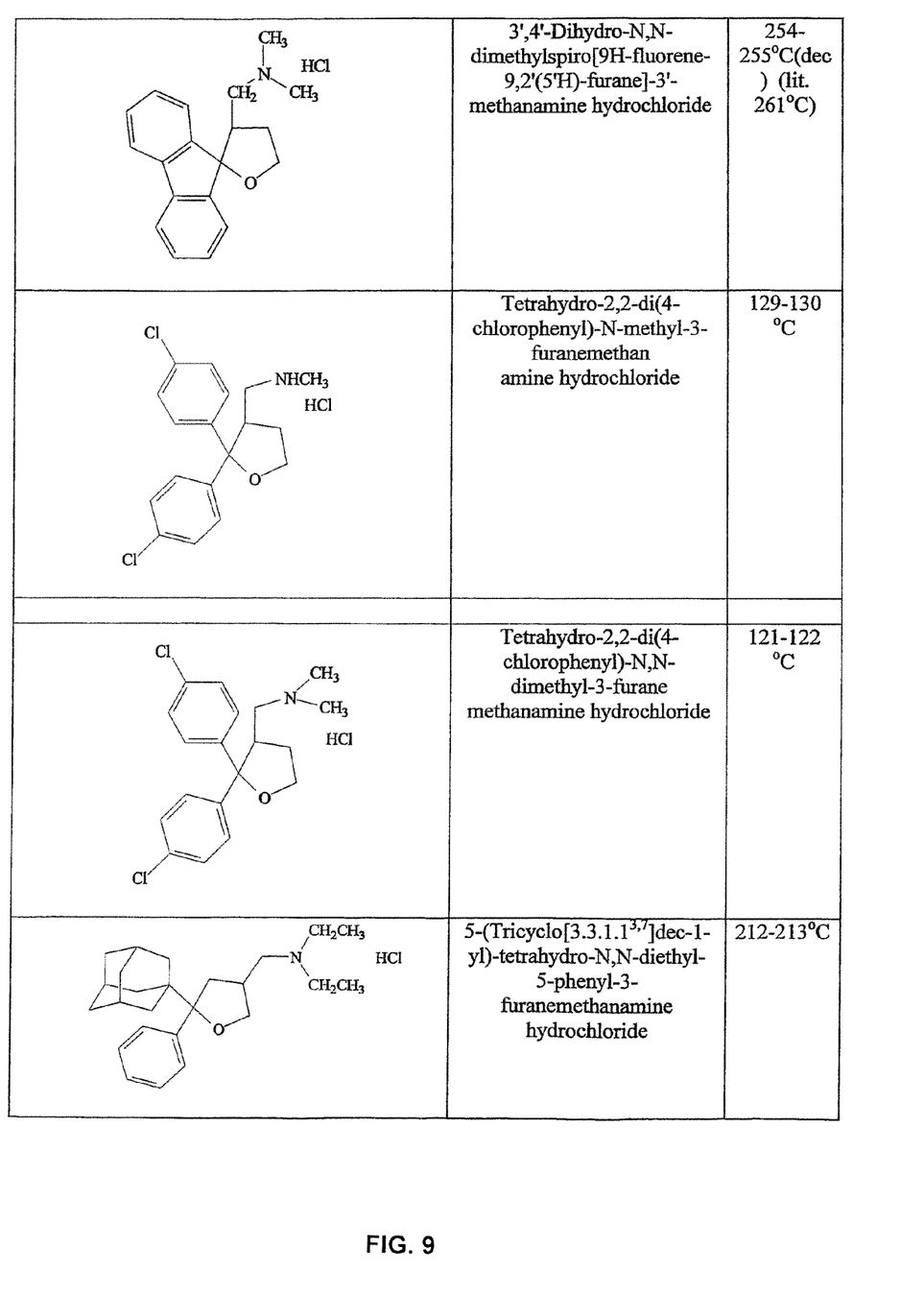
FIG. 9 is a structural representation of 3',4'-Dihydro-N,N-dimethylspiro[9H-fluorene-9,2'(5'H)-furane]-3'-methanamine hydrochloride, Tetrahydro-2,2-di(4-chlorophenyl)-N-methyl-3-furanemethan amine hydrochloride, Tetrahydro-2,2-di(4-chlorophenyl)-N,N-dimethyl-3-furane methanamine hydrochloride, 5-(Tricyclo[3.3.1.1$^{3,7}$]dec-1-yl)-tetrahydro-N,N-diethyl-5-phenyl-3-furanemethanamine hydrochloride.
Figure 10:
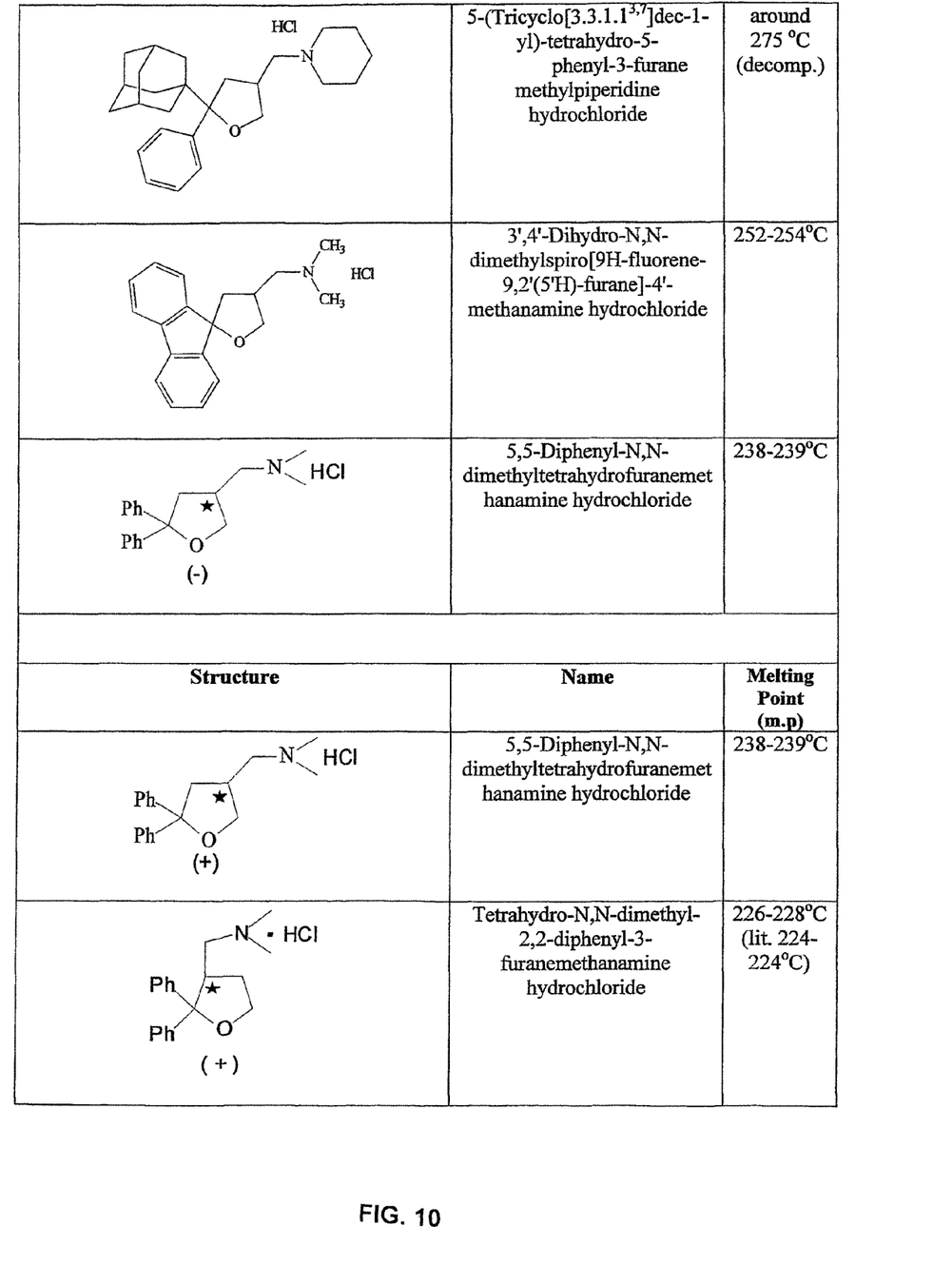
FIG. 10 is a structural representation of 5-(Tricyclo[3.3.1.1$^{3,7}$]dec-1-yl)-tetrahydro-5-phenyl-3-furane methylpiperidine hydrochloride, 3',4'-Dihydro-N,N-dimethylspiro[9H-fluorene-9,2'(5'H)-furane]-4'-methanamine hydrochloride, 5,5-Diphenyl-N,N-dimethyltetrahydrofuranemet hanamine hydrochloride, 5,5-Diphenyl-N,N-dimethyltetrahydrofuranemet hanamine hydrochloride, Tetrahydro-N,N-dimethyl-2,2-diphenyl-3-furanemethanamine hydrochloride.
Figure 11:
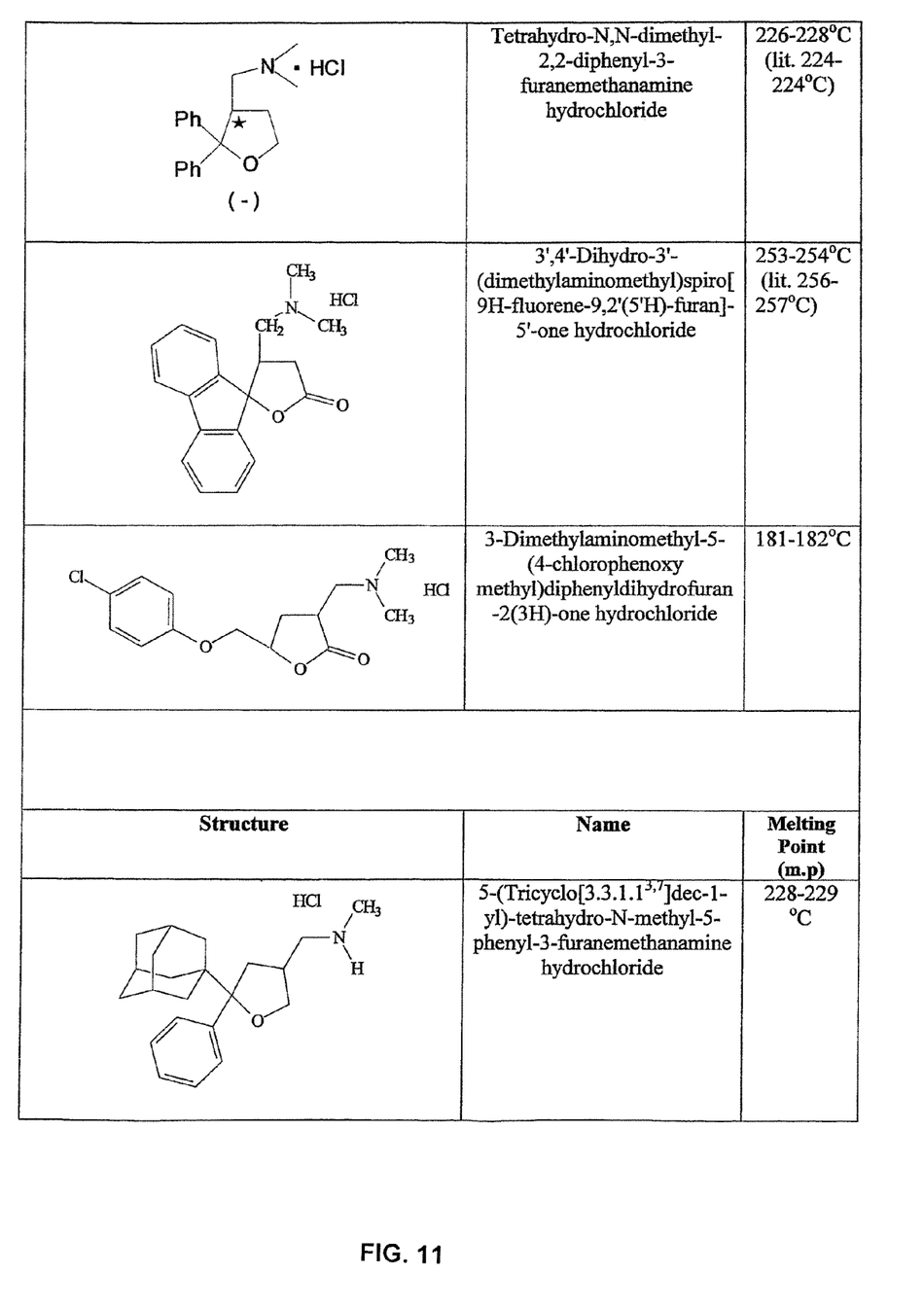
FIG. 11 is a structural representation of Tetrahydro-N,N-dimethyl-2,2-diphenyl-3-furanemethanamine hydrochloride, 3',4'-Dihydro-3'-(dimethylaminomethyl)spiro[9H-fluorene-9,2'(5'H)-furan]-5'-one hydrochloride, 3-Dimethylaminomethyl-5-(4-chlorophenoxy methyl) diphenyldihydrofuran-2(3H)-one hydrochloride, 5-(Tricyclo[3.3.1.1$^{3,7}$]dec-1-yl)-tetrahydro-N-methyl-5-phenyl-3-furanemethanamine hydrochloride.
Figure 12:
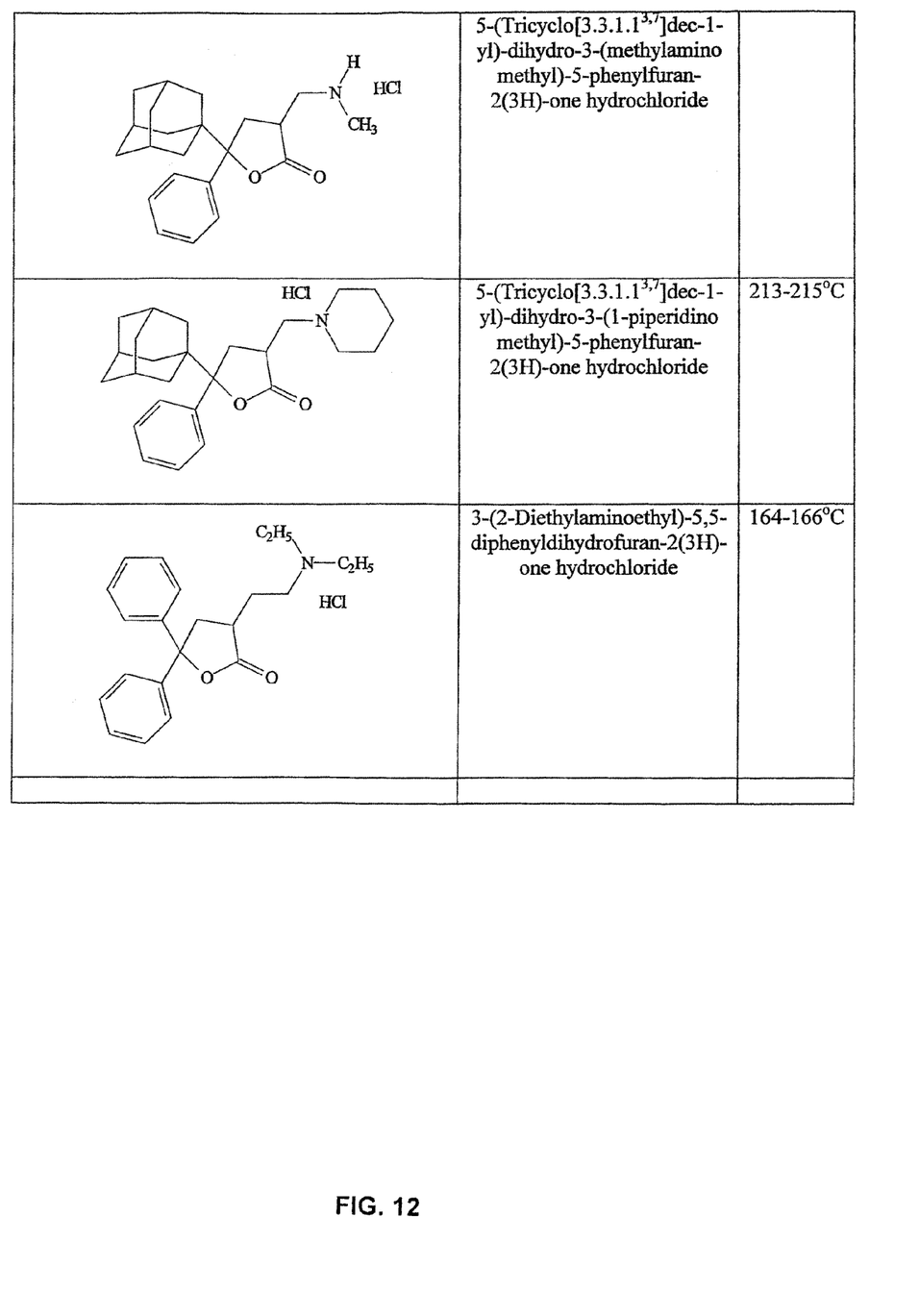
FIG. 12 is a structural representation of 5-(Tricyclo[3.3.1.1$^{3,7}$]dec-1-yl]-dihydro-3-(methylamino methyl)-5-phenylfuran-2(3H)-one hydrochloride, 5-(Tricyclo[3.3.1.1$^{3,7}$]dec-1-yl)-dihydro-3-(1-piperidino methyl)-5-phenylfuran-2(3H)-one hydrochloride, 3-(2-Diethylaminoethyl)-5,5-diphenyldihydrofuran-2(3H)-one hydrochloride.

The present invention concerns the prototypical σ receptor ligands (Mono- or Dialky-Iaminoalkyl)-$_\gamma$-butyrolactones (AL), their analogues aminotetrahydrofuranes (AE), with various substitutes: phenyl-, diphenyl-, phenoxymethyl, fluorenyl or adamantyl, the (1-adamantyl)phenyl(s) alkylamines-(AdBAA), the N,N Dialkyl α-[(adamantyl-1)benzyloxy-2] alkylamines-(AdBOAA) and the 3-cyclopentyl-adamantyl-amines or alkylamines or alkyiphenyl amines (AdCP), halogenated, or methoxylated on their substitutes and their pharmaceutically acceptable salts of the racemics, enantiomers and diastereoisomers and also the characterized by the inventor as σ ligands generics Quinacrine (QNC), Methylene blue (MB), Astemizole (AST) and their related analogues, with prototypical anticancer and antimetastatic properties associated with analgesic activity against the neuropathic pain, generally, and also those induced by the clinically used anticancer drugs. At lower doses the above compounds and drugs exhibited prototypical cytoprotective properties associated with cytoregenerative activity developed by antagonism of the endoplasmic reticulum stress (ER stress) via activation of the sigma receptors in the connecting membrane between ER and mitochondrion.

The present invention concretize the concept of bio-modulatory activity with the original σ-receptor ligands AL, AE, AdBAA, AdBOAA, AdCP and the, recently characterized by the inventor as a ligands, generics: QNC,MB,AST and also their related analogues with a new and sophisticated mechanism including the disclosed orthosteric and allosteric modulations but, principally, the activation of their σ-1 receptors (chaperones) in the dysregulated cells of the degenerative diseases characterized by hyper activation of the apoptotic process or, in cancer cells, the deactivation of these chaperones, at high doses of the above ligands, where they abolish the defensive inhibition of the apoptotic processus in the cancer cells.

In vitro and in vivo experiments clearly demonstrated the principal interaction of AL, AE, AdBAA, AdBOAA, AdCP and also QNC,MB and AST over the σ-1, σ-2 receptors from sub-nanomolar up to micromolar levels of affinity along with their regulatory roles over the G-protein coupled receptors (GPCRs) and sodium (Na), calcium (Ca), potassium (K) and chloride (Cl) ion channels and, principally, on the pathways of the ER and mitochondrion which determinate the protection of the cells in the degenerative diseases and the apoptosis of the cancer cells.

Thus, in contrast to the precedent patents of the inventor, the above invention displaced the area of the putative application of these molecules from the symptomatic to the therapeutic use because, specially for the cytoprotecting and cytoregeneratingi properties of the following claims the activity of the molecules concern the intracellular targets and pathways of pathogenesis and not the activity of superficial cell membrane receptors, as it is usually the case with the symptomatic drugs: neuroleptics, anti depressive drugs and cholinergics for, respectively, psychosis, depression and Alzheimer.

On the other hand, recent experiments in vivo demonstrated the prototypical profile of the above a ligands which associated the anticancer activity with the antagonism of pain or neuropathic pain and also those originated from the anticancer treatments with the clinically used anticancer drugs and specially with taxanes, platinum agents and vicristine. Thus, the invention of this prototypical activity supported the synergistical use of the above a ligands with the clinically active anticancer drugs—as it was recently demonstrated with xenograft experiments on SCID mice and also, with neuropathic pain protocols, on CD-1 and Balb-C mice—with simultaneous antagonism, by the above a ligands, of the painful effects and disability induced by the clinically used anticancer drugs.

Finally, their ability to regulate cellular apoptotic processes, through ER-mitochondrial σ-1 and σ-2 receptors, associated with the stereochemical re-articulation of the membrane sphingolipides, induced by the above ligands, supported the antiviral activity of the above compounds (more specially those containing adamantyl(s)), which was demonstrated experimentally in vitro.

EXAMPLES

A) Sigma (σ)-1 Agonists with Bio-Modulatory Properties and with Antagonistic Action on the Apoptotic Processes of the Cells AE14: Tetrahydro-N,N,-Dimethyl-5,5-Diphenyl-3-Furanomethanamine AE14 is a selective ligand for σ-1 receptors with a nanomolar affinity (pKi=7.6) while the affinity for σ-2 receptors is more than 100 times lower [over 10 micro-Moles (10 μM): pKi<5]. The above molecular profile is the basis for AE14 modulatory role over the G-protein coupled receptors (GPCRs) and its pharmacological properties: anti-amnesic action (antagonistic action against scopolamine and dizocilpine (MK-801) induced amnesia or amyloid peptide β25-35 (Aβ25-35), at low doses (from 0.03 mg/kg administered per os (po), in mice). This unique new profile of AE14: anti-apoptotic via agonistic sigma-1 regulation of the volume regulated chloride channels (VRCC), anti-oxidative stress via agonistic action on the sigma-1 receptors of the ER-mitochondrion.

Recent experiments amplified the above disclosed results and demonstrated the putative cytoprotective and cytoregenerative activity of AE14 and the relative analogues, by triggering the activity of the a chaperones in the ER-mitochondrion, in protocols of acute or chronic cellular stress (in vitro and in vivo on mice) using oligopeptides or streptozocin which initiate ER stress and cytotoxic activity by apoptosis. In the above protocols, AE14 antagonized the ER stress extending its application area to the intimate causes: dysregulation of the σ chaperones regulated alarm pathways to mitochondrion, and therefore to all the cytodegenerative diseases.

Tetrahydro-N,N-Dtiviethyl-2,2-Dinienyl-3-Furanomethanamine

Similar pharmacological profile as to AE14: smaller affinity for σ-1 receptors (pKi=6.3) and with no affinity for σ-2 receptors.

Therefore, AE37, as a selective σ-1 agonist with anti-apoptotic action, was recently studied in vitro and in vivo on mice in protocols of chronic ER and cellular stress and exhibited high anti-apoptotic properties and putative cytoprotective and cytoregenerative activity.

AE37Met:Tetrahydro-N-Methyl-2,2-Diphenyl-3-Furanomethanamine

AE37 Met is the only metabolite of AE37 and is slightly more active than AE37 for the properties mentioned above but it mainly concerns the cytoprotective action, especially against acute intracellular (ER-mitochondrion) stress and then against the ischemic syndromes (brain, heart), in relevance with its exceptional protection against ER-mitochondrion anoxia and oxidative stress caused by pentylenetetrazole (PTZ), in vitro or in vivo, on mice, following its protection against the PTZ-induced tonic crises.

B) Weak σ-1 Agonists or σ-1 Antagonists with Agonistic σ-2 Component and Agonistic Action to the Apoptotic Processes of the Cells

The following molecules are representatives of the chemical families that concern the present invention:
1) AdAL: DIHYDRO-4-(D1METHYLAMINOMETHYL) SPIRO {FURANE-2(5H),2'-TRICYCLO[3.3.1.1$_{3,7}$]DECAN}-5-ONE 6—
2) AdAE: (DIHYDRO-4-(DIMETHYLAMINOMETHYL) SPIRO {FURANE-2(3H),2'-TRICYCLO[3.3.1.1$_{3,7}$]DECANE}
3) AdPhAL: 5-(TRICYCLO[3.3.1.1$_{3,7}$]DEC-1-YL)-DIHYDRO-3-[DIMETHYLAMINOMETHYL)-5-PHENYLFLTRAN-2(3H)-ONE—
4) AdPhAE: 5-(TRICYCLO[3.3.1.1$_{3,7}$]DEC-1-YL)-TETRAHYDRO-N,N-DIMETHYL-5-PHENYL-3-FURANEMETHANAMINE—
5) AL142Me: (α-(DINIETHYLAMENOETHYL)-$_{\gamma,\gamma}$-DIPHENYL-$_\gamma$-BUTYROLACTONE)
6) AdBPA: $_\gamma$-(1-ADAMANTYL)PRENYL-N,N-DIMETHYLPROPANAMINE
7) AdBPP: $_\gamma$-(1-ADAMANTYL)PHENYL-PROPYLPIPERIDINE
8) AdBOPP: [α-(ADAMANTYL-1)BENZYLOXY-2]PROPYLPIPERIDINE
9) AdBOEA (Me): N,N DIMETHYL-α-(ADAMANTYL-1) BENZYDRYLOXY-2-ETHYLAMINE
10) -Ad(Me)CP: 3-CYCLOPENTYL-N-METYL-1-TRICYCLO[3.3.1.1$_{3,7}$]DECANEMETHANAMINE
11) Quinacrine (QNC)
12) Methylene blue (MB)
13) Astemizole (AST)
(see also, in appendix, undescribed derivatives of the above chemical families)

All molecules present strong chemical affinities (sub-nanomolar to micromolar) for α-1 receptors with antagonistic action (except AdAE and AdPhAE which are weak agonists) and with nanomolar to micromolar affinities for α-2 receptors and agonistic action. Therefore, all molecules above and their derivatives are pro-apoptotic and only at very low concentrations or doses are anti-apoptotic. All molecules above are toxic to the cancer cells: colorectal, prostate, ovarian renal, pancreas, lung, gliomas, glioblastomas leukemia, lymphomas, melanomas, sarcomas and hepatoma, with antiproliferative and cytotoxic concentrations usually lower than 10 microMolar (μM), for more than 50 of the above derivatives. Outstanding cytotoxicity, in vitro and the corresponding in vivo anticancer activity in mice xenografts, is for the first time disclosed for QNC and AST: 3.0-5.0 μM for all the above cancer cells and an outstanding in vivo activity of QNC on primary (drug resistant) melanoma, in which Dacarbazine is inactive, or MB: lower than 1.0 μM in vitro for primary (drug resistant) melanoma or leukaemia and lung and close to 2.0 μM in breast, colon and glioblastomas confirmed in vivo, specially in primary melanoma. All these molecules make excellent and prototypical anticancer drug candidates due to their aptitude to, simultaneously, antagonize the neurogenic and, more exceptional, the neuropathic and inflammatory pain as recently demonstrated by the appropriate experimental protocols: hot plate, formalin, von Frey fibers and, principally, the protocols based on previous administration of paclitaxel, oxaliplatine and streptozocin which concern more specifically the neuropathic pain originating from chronic administration of anticancer drugs, from diabetes or other neurotoxic stimulus. The pharmacological profile of the above molecules is totally prototypical and original giving the possibility of a therapeutic synergy with the clinically used anticancer drugs with simultaneous antagonism and protection against the most grave secondary effects i.e., neuropathic pain and disability induced by the clinically used anticancer drugs.

1) Pouli N., Fytas G., Foscolos G., Kolocouris N., Marakos P., and Vamvakides A. Synthese et etude pharmacologique des adaman-tylbenzenepropanamines et propenamines. Annales Pharmaceutiques Francaises, 1995, 53, No 4, pp 163-169 33]
2) Fytas G., Marakos P., Kolocouris N., Foscolos G., Pouli N., Vamvakides A., Ikeda S., De Clercq E. 3-cyclopentyl-1-aclamantamines and adamantanemethanamines. Antiviral activity evaluation and convulsion studies. Farmaco 1994, 49, No 10, pp 641-647 [0034]
3) Vamvakides Alexandre: Tetrahydro-N, N-dimethyl-2,2-diphenyl-3-furanemethanamine, its enantiomers and their pharmaceutically acceptable acid addition salts. WO97/30983 and patent 1002616 (GR)

The invention claimed is:
1. A method of treating melanoma in a subject comprising administering in a subject in need thereof a therapeutic amount of a first compound shown here and a therapeutic amount of a second compound selected from the group consisting of quinacrine, methylene blue, or astemizole.
2. The method of claim 1 wherein the second compound is quinicrine.
3. The method of claim 1 wherein the second compound is methylene blue.
4. The method of claim 1 wherein the second compound is astemazole.
5. A method of treating melanoma in a subject comprising administering in a subject in need thereof a therapeutic amount of a first compound shown here and a therapeutic amount of a second compound selected from the group consisting of quinacrine, methylene blue, or astemizole.
6. The method of claim 5 wherein the second compound is quinicrine.
7. The method of claim 5 wherein the second compound is methylene blue.
8. The method of claim 5 wherein the second compound is astemazole.
9. A method of treating melanoma in a subject comprising administering in a subject in need thereof a therapeutic amount of a first compound shown here and a therapeutic amount of a second compound selected from the group consisting of quinacrine, methylene blue, or astemizole.
10. The method of claim 9 wherein the second compound is quinicrine.
11. The method of claim 9 wherein the second compound is methylene blue.
12. The method of claim 9 wherein the second compound is astemazole.
13. A method of treating melanoma in a subject comprising administering in a subject in need thereof a therapeutic amount of a first compound shown here and a therapeutic amount of a second compound selected from the group consisting of quinacrine, methylene blue, or astemizole.
14. The method of claim 13 wherein the second compound is quinicrine.
15. The method of claim 13 wherein the second compound is methylene blue.
16. The method of claim 13 wherein the second compound is astemazole.

* * * * *